(12) United States Patent
Jeschonek et al.

(10) Patent No.: US 6,771,913 B2
(45) Date of Patent: Aug. 3, 2004

(54) APPARATUS AND METHOD FOR ACQUIRING THE NATURE OF A TONER PARTICLE LAYER AND THE MOISTURE CONTENT OF A CARRIER MATERIAL IN A PRINTER OR COPIER

(75) Inventors: Markus Jeschonek, München (DE); Peter Möstl, Altdorf-Pfettrach (DE); Wolfgang Schullerus, Raubling (DE); Alfred Zollner, Eitting (DE)

(73) Assignee: Oce Printing Systems GmbH (DE)

( * ) Notice: Subject to any disclaimer, the term of this patent is extended or adjusted under 35 U.S.C. 154(b) by 0 days.

(21) Appl. No.: 10/271,041

(22) Filed: Oct. 15, 2002

(65) Prior Publication Data

US 2003/0091355 A1 May 15, 2003

(30) Foreign Application Priority Data

Oct. 19, 2001 (DE) .......................................... 101 51 703

(51) Int. Cl.[7] .............................................. G03G 15/00
(52) U.S. Cl. .......................... 399/49; 324/663; 324/671
(58) Field of Search .............................. 399/49, 60, 72, 399/45; 324/658, 686, 662, 663, 665, 671

(56) References Cited

U.S. PATENT DOCUMENTS

| | | | | |
|---|---|---|---|---|
| 4,245,022 A | | 1/1981 | Sadamatsu et al. ...... 430/108.1 |
| 4,610,530 A | * | 9/1986 | Lehmbeck et al. ........... 399/45 |
| 4,706,032 A | | 11/1987 | Allen et al. .................... 399/62 |
| 4,860,924 A | | 8/1989 | Simms et al. ................. 222/56 |
| 4,935,776 A | | 6/1990 | Fukui .......................... 399/31 |
| 5,500,716 A | | 3/1996 | Morishita et al. ............. 399/35 |
| 5,657,114 A | | 8/1997 | Kitajima et al. .............. 399/71 |
| 5,694,223 A | | 12/1997 | Katori et al. ................ 358/300 |
| 5,918,085 A | | 6/1999 | Rollins et al. ................ 399/27 |
| 5,987,269 A | | 11/1999 | Allen et al. .................... 399/27 |
| 6,021,294 A | | 2/2000 | Schmid et al. ............. 399/258 |
| 6,486,680 B1 | * | 11/2002 | Mull .......................... 324/686 |
| 2002/0044785 A1 | * | 4/2002 | Luxem ........................ 399/49 |

FOREIGN PATENT DOCUMENTS

| | | |
|---|---|---|
| DE | J196 43 611 | 4/1998 |
| JP | 59131104 | 7/1984 |
| JP | 04077604 | 3/1992 |
| JP | 11133721 | 5/1999 |

OTHER PUBLICATIONS

Xerox Disclosure Journal—1988 vol. 13, No. 4 Jul./Aug.— C. A. Radulski

* cited by examiner

*Primary Examiner*—Arthur T. Grimley
*Assistant Examiner*—Ryan Gleitz
(74) *Attorney, Agent, or Firm*—Schiff Hardin LLP

(57) ABSTRACT

An apparatus and method are provided for acquiring the nature of a toner particle layer in a printer or copier. An apparatus and a method are also provided for acquiring the moisture content of a carrier material in a printer or copier. A toner particle layer is transported forward between two capacitor plates arranged next to one another and a cooperating electrode. In a first switch status, the first and the second capacitor plate are charged with voltages opposite one another. In a second switch status, the first and the second capacitor plate are electrically connected to one another, whereby the remaining charge is identified and conclusions about the nature of the toner layer are drawn therefrom.

19 Claims, 16 Drawing Sheets

APPARATUS AND METHOD FOR ACQUIRING THE NATURE OF A TONER PARTICLE LAYER AND THE MOISTURE CONTENT OF A CARRIER MATERIAL IN A PRINTER OR COPIER

BACKGROUND OF THE INVENTION

The invention is directed to an apparatus and a method for acquiring the nature of a toner particle layer in a printer or copier. The toner particle layer is contained in the dielectric of a capacitor at least at times. Electrical properties of the capacitor can be used to draw conclusions about the nature of the dielectric and, thus, about the nature of the toner particle layer. The invention is also directed to an apparatus and a method for acquiring the moisture content of a carrier material in a printer or copier.

For generating a visible image in electrographic printer or copier devices, toner is applied on a carrier medium and fixed thereon. A latent charge image is generated on an image-generating medium, for example on a photoconductor, and is subsequently inked with toner. The toner image is subsequently transferred onto a carrier material and fixed thereon. The obtainable print quality is particularly dependent on the inking degree of the print or toner image and, thus, on the amount of colorant transferred on a recording medium, i.e. on the transferred toner. In, for example, the presentation of a solid area, rastered half-tone areas, lines, characters and the like, the inking degree must be kept within certain limits. The first inking degree of a print or toner image must therefore be measured and the quantity of colorant or toner to be applied must subsequently be set with the assistance of a regulating system in conformity with the measured result. The regulating event can also be repeated at certain time intervals according to the demands made of the print quality.

For example, surface regions are designationally inked—these being referred to as print or toner marks—for determining the inking degree of print or toner images.

The determination of the inking degree of print or toner marks can be undertaken directly on a recording medium and/or an image-generating medium such as, for example, a photoconductor drum or an applicator element.

For achieving a required printing quality, the amount of toner applied in the inking of the latent charge image must be kept exactly within predetermined limits since, for example, an area to be inked black only appears as deep black when enough toner is applied. On the other hand, too much toner dare not be applied given, for example, thin lines lying close to one another since the lines otherwise bleed into one another.

For economical as well as ecological reasons, it is not meaningful or justifiable to apply more toner on the photoconductor for an area to be inked than is absolutely necessary or—expressed in other words—only as much toner as required for the respectively desired inking degree should always be applied insofar as possible. Optoelectrically functioning sensor systems are known for measuring the inking degree of print or toner images in the form of toner marks. Upon employment of such systems, a toner mark is irradiated with visible or infrared light. On the basis of different reflection and absorption properties of toner marks that are dependent on the amount of toner contained in the toner mark, the intensity of the reflected or transmitted light is measured by means of an optoelectrical sensor system and the inking degree is subsequently identified. The measured result of optoelectrically operating sensor systems for determining the inking degree of toner marks, however, is also dependent on the optical properties of the medium on which the toner mark is applied. Print image mismatches thus can already occur given employment of different paper grades. Similar print image mismatches can occur, for example, due to fluctuations in the photoconductor charges.

Further, the reflected or transmitted light quantity decreases only until the surface elements of the toner mark have been covered gap-free with toner. Given completely absorbent toner material, a multi-layer tonering of the toner mark that increases thereafter no longer leads to changes in the reflected/absorbed light quantity and, thus, of the electrical signal. Optoelectrical sensors can thus not detect a further increase in the layer thickness. Different reflection and absorption properties are also present given different toner brands and given toners with different colors. An optoelectrical sensor must therefore be specifically adapted to the toner respectively employed or to each colored toner. These adaptations are very time-consuming and cost-intensive. Optoelectrical sensor systems deliver only inadequate measured results for specific colored toners.

DE 196 43 611 A1 discloses a method and an apparatus for determining an inking degree of tonered areas in a printer or copier device. For determining the inking degree, measurement is carried out relative to a non-tonered carrier medium as well as relative to a toner mark using two capacitive sensors arranged transversely relative to the conveying direction of a carrier material. The layer thickness of the toner layer is identified from the two measured values. However, imprecise measured results are already obtained given slight adjustments imprecisions of the sensor and given a topical variation of the physical properties of the carrier medium, a high print quality being no longer assured as a result thereof. Further devices and methods for determining the inking degree are disclosed by U.S. Pat. Nos. 6,021,294, 5,987,269, 5,918,085, 5,694,223, 5,657,114, 5,500,716, 4,935,776, 4,860,924, 4,706,032 and 4,245,022.

SUMMARY OF THE INVENTION

An object of the invention is to specify a simply constructed, cost-beneficial apparatus and a method that is simple to implement and by means of which the nature of a toner particle layer is relatively precisely determined. Another object of the invention is to specify a simply constructed apparatus and a method that is simple to implement and with which the moisture content of a carrier material is determined in a simple way.

According to the invention, a nature of a toner particle layer in a printer or copier is acquired by arranging a first capacitor plate and a second capacitor plate next to one another and lying opposite at least one cooperating electrode to form a first capacitor and a second capacitor. A layer that contains toner particles is arranged in a region between the two capacitor plates and the cooperating electrode. The two capacitors are charged with voltages opposite one another in a first switch status. In a second switch status, the first and the second capacitor plates are electrically connected to one another and a remaining charge is determined after a charge compensation. Conclusions about the nature of the toner layer are drawn from the remaining charge.

DESCRIPTION OF THE PREFERRED EMBODIMENTS

Figure 1:
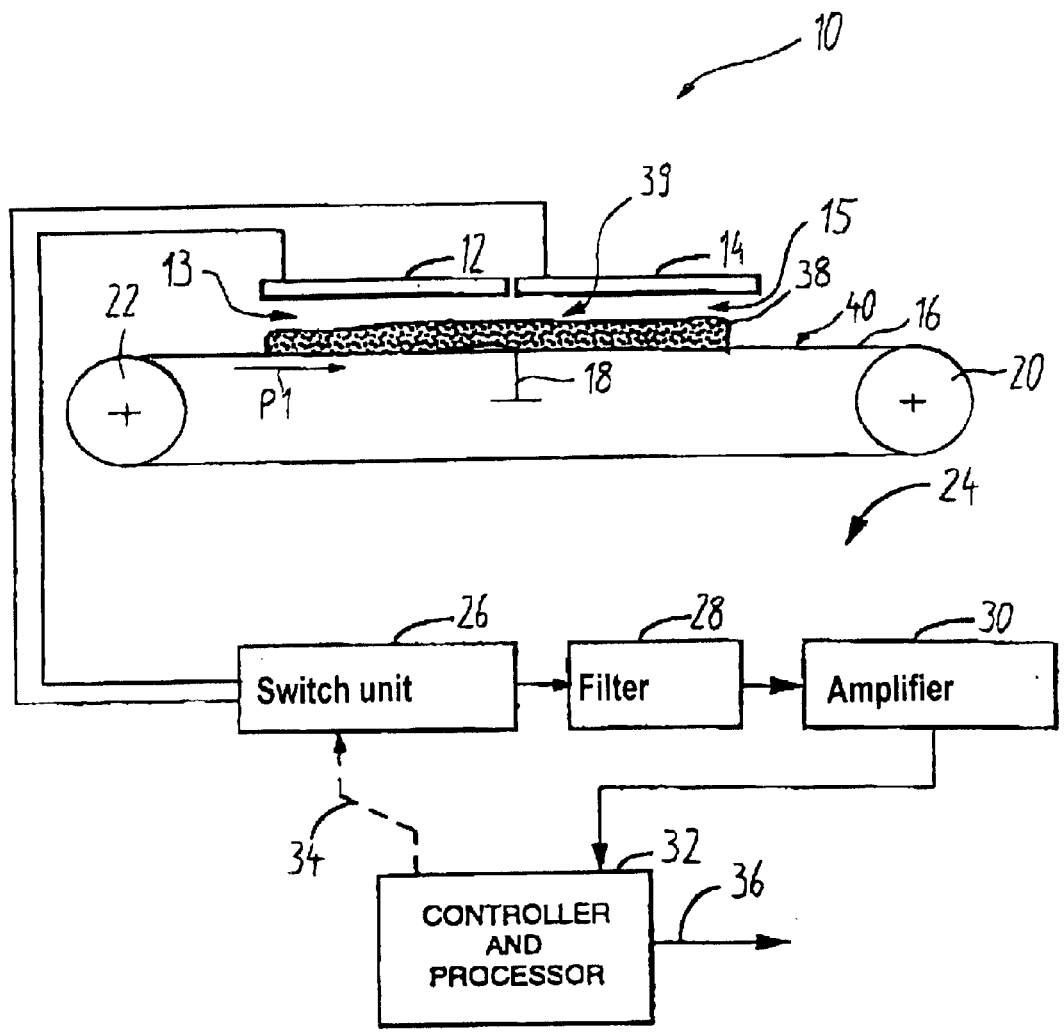
FIG. 1 shows the fundamental structure of an apparatus for determining the layer thickness of a toner mark on a carrier material.

For the purposes of promoting an understanding of the principles of the invention, reference will now be made to the preferred embodiment illustrated in the drawings and specific language will be used to describe the same. It will nevertheless be understood that no limitation of the scope of the invention is thereby intended, such alterations and further modifications in the illustrated device, and/or method, and such further applications of the principles of the invention as illustrated therein being contemplated as would normally occur now or in the future to one skilled in the art to which the invention relates.

The apparatus for acquiring the nature of a toner particle layer in a printer or copier contains two capacitors. In a first switch status, these capacitors are charged with voltages opposite one another. In a second switch status, the first and the second capacitor plate are electrically connected to one another, whereby the remaining charge is identified. The apparatus has a simple structure and can be cost-beneficially manufactured. As a result of the toner particle layer contained in the dielectric, a different dielectric of the two capacitors causes a remaining charge. Conclusions about the nature and/or about a change in the nature of the toner layer can be drawn from the remaining charge. The nature of the toner layer can thereby be the layer thickness, the density or the moisture content of the toner particle layer. The layer thickness of the toner layer is a determining factor for the inking degree of the print image. The type of toner, for example the toner color, can be determined with the assistance of the density of the toner layer. The moisture content, for example, provides information about the consistency of the toner material. What is thereby achieved is that property parameters of the toner particle layer that are critical for the quality of the print result are acquired and are used for control and/or regulating processes in the printer, as a result whereof a high print quality is assured.

The operation of the capacitors in two switch statuses also enables slight changes of the dielectric to be detected and interpreted as a charge difference. A charge carrier exchange of the two capacitors already occurs in the second switch status due to the short-circuit of the capacitor plates. An evaluation circuit need only evaluate the remaining charge. The difference formation of the charges of the capacitors in the second switch status occurs in a simple way by means of the charge carrier exchange. The charging and the discharging of the capacitors occur successively as a result of the first and second switch status, as a result whereof high-precision measured results are obtained with little measuring expense. The nature of the toner particle layer can be exactly determined with the assistance of these measured results.

For example, the application of toner can be controlled or regulated with the assistance of these measured results such that the inking degree of a toner image is kept within a prescribed, narrow range of tolerance. As a result thereof, a high image quality of the print product is assured and the toner consumption is optimized at the same time.

In one embodiment, the toner layer is transported forward, i.e. conveyed through, between the capacitor plates and the cooperating electrode. When, for example, the capacitor plates are successively arranged in moving direction, then the change in capacitance of the two capacitors occurs successively. As a result thereof, the measured result in this embodiment is only insignificantly falsified by fluctuations in the photoconductor charges. Further, the layer thickness of the toner particle layer can still be exactly determined given toners with different colors since the influence of the different physical properties of the differently colored toner layers has only a slight influence for determining the layer thickness of the toner particle layer.

In another embodiment, the remaining charge generates a value of current that serves as a signal value. In a development of this embodiment, the current signal values are converted into voltage signal values. A current corresponding to the remaining charge can be generated from the remaining charge in a simple way. This current is directly proportional to the remaining charge of the two capacitors. After the conversion of the current signal values and voltage signal values, a further-processing of the voltage signal values is possible in a simple way, for example with the assistance of operational amplifiers or digital signal processors. Further, voltage signal values can be distributed in a simple way and thus be supplied to a plurality of signal inputs of evaluation circuits in an uncomplicated way.

In one development, a signal processing unit amplifies the signal values generated from the remaining charge and filters these with the assistance of a band-pass filter. What is thereby achieved is that signal disturbances that are caused, for example, by the switching of the first and second signal status are simply filtered out with the assistance of a band-pass filter or with the assistance of other known filters. The nature of the toner layer can be exactly determined with the assistance of the filtered signal values. For further-processing, the signal is amplified after the filtering. The filtering, amplification and evaluation preferably occurs with the assistance of a digital signal processor, as a result whereof no further assemblies need be provided for the signal editing.

In another embodiment, the toner density and/or the thickness of the toner layer is determined with the assistance of pre-set comparison values. This makes a simple evaluation possible that requires only a simple evaluation circuit. For example, such an evaluation circuit can contain a comparator.

In another development of the invention, the duration of the first and of the second switch status is approximately the same, and the switch statuses are switched with a frequency in the range between 300 kHz and 1 MHz. The charging and discharging of the capacitors thereby occurs such that signals that are easy to interpret are generated. The apparatus is thus operated according to what is referred to as a switched capacitor method. Arrangements having a switching frequency in the range from 300 kHz through 1 MHz can be manufactured of cost-beneficial components, whereby high-precision measured results can be achieved.

When, for example, electronic switch elements are utilized in other embodiments, the switch statuses can be switched with a frequency of up to 3 MHz. The switching frequency is only limited by the possible switching frequency of available switch elements. The switched capacitor method can also be implemented with high switching frequencies. Further, the duration of the switch statuses, i.e. what is referred to as the pulse duty factor, can be varied in order to further reduce disturbing influences. The duration of the switch statuses can be pre-set to between 10 and 90% of the total duration of the two switch statuses, as a result whereof further disturbing influences are avoided, dependent on the application.

In another advantageous development, the carrier element on which the toner mark is applied contains conductive elements, whereby the carrier element forms the cooperating electrode. What is thereby achieved is that no separate cooperating electrode is required; instead, for example, a photoconductor belt, a transfer belt, an applicator belt, an applicator drum, a photoconductor drum or a transfer drum can be used as the cooperating electrode. The carrier element can thereby also be pre-set to an electrical potential, for example a reference potential, in that the carrier element is electrically conductively connected to this potential.

In another embodiment, a signal processing unit acquires the signal values of the remaining charge of an entire belt pass or of an entire drum revolution of the belt cleaned of toner particles or of the drum cleaned of toner particles and stores these signal values with the allocation to the respective drum or, respectively, belt position in a memory area of the signal processing unit. During a second operating phase of the printer or copier, the difference between current and stored signal value is formed for each stored drum or, respectively, belt position, whereby the signal processing unit determines the nature of the toner layer with the assistance of the difference. The first operating phase is preferably activated following turn-on or given the initialization as well as given maintenance work performed on the printer or copier.

After the determination of the signal values of at least one drum or belt revolution, the second operating phase is automatically activated. No toner marks are generated during the first operating phase. What is thereby achieved is that changes in signal value as a consequence of different nature of the carrier material can also be compensated in that they are taken into consideration in the evaluation of the signal values. Thus, for example, the difference value from measured signal value and stored signal value can be used for the further-processing. Remaining contamination and irregularities in the carrier material can thus also be taken into consideration in the determination of the layer thickness of the toner mark, as a result whereof the layer thickness can be even more exactly determined.

A method is provided for acquiring the nature of a toner particle layer in a printer or copier whereby two capacitors are provided whose electrical properties are used as criterion for the nature of the toner particle layer. In a first switch status, the capacitors are charged with opposite voltages. In a second switch status, the two capacitors are short-circuited, as a result of which a charge carrier compensation occurs. The remaining charge is evaluated as measured signal. With this method, it is simply and cost-beneficially possible to exactly identify the nature of the toner layer, for example of a toner mark. With, for example, the assistance of the identified nature of the toner layer, a control and/or a regulation can control or regulate the inking, i.e. the layer thickness, of a latent charge image with toner. Involved setting and matching work for adapting a measurement arrangement for the implementation of the method to, for example, different carrier materials and different toner parameters are not necessary in this method.

In an apparatus for acquiring the moisture content of a carrier material in a printer or copier, the capacitor is charged with a pre-set voltage in a first switch status. The capacitor plate is connected to an evaluation unit in a second switch status. The remaining charge is thereby identified. Conclusions about the moisture content of the carrier material are drawn from the remaining charge. What is thereby achieved is that the moisture content of the carrier material can be relatively precisely determined with the assistance of simple apparatus. Corresponding to the moisture content, the moisture content of the carrier material can then be set to a value in a pre-defined range, for example with the assistance of a drying device.

Further, the moisture content of the carrier material can also be used for controlling the fixing performance of a fixing unit that fixes the toner image transferred onto the carrier material on the carrier material. As a result thereof, it can be assured that adequate fixing energy in order to fix the toner image with high quality is supplied even given a high moisture content of the carrier material. Given carrier material with low moisture content, the fixing energy can then be correspondingly reduced in order to prevent the carrier material from being damaged.

In another development, the moisture content of the carrier material is measured before the fixing event and after the fixing event, whereby the fixing energy of the fixing unit is determined from the moisture difference of the two measurements. Given a single sheet or single page processing, the moisture content of the sheet or of the page can be determined by the same apparatus. As a result thereof, the fixing performance of the fixing unit can be identified and regulated, as a result of which the high-quality fixing of the toner images on the carrier material is assured.

A method for acquiring the moisture content of a carrier material in a printer or copier can be implemented in a simple way without great expense, whereby the moisture content of the carrier material is exactly determined. With the assistance of the identified moisture content, for example, the parameters of the printer or copier can be adapted in order to obtain optimum printing results at the corresponding moisture content of the carrier material.

FIG. 1 shows an apparatus for acquiring the nature of a toner particle layer 38 in an electrographic printer or copier. The layer thickness of the toner layer 38 is determined with the assistance of the apparatus 10. The toner layer 38 has been generated on a photoconductor belt 16 with the assistance of an exposure and development unit (not shown). The toner layer 38 forms a toner mark 39. The photoconductor belt 16 is implemented as a circulating belt that is deflected with the assistance of the deflection drums 20, 22. The photoconductor belt 16 contains electrically conductive constituents that are electrically conductively connected to a reference potential 18. The photoconductor belt 16 has a top surface 40 on which the toner layer 38 is situated. A first capacitor plate 12 and a second capacitor plate 14 are arranged parallel to the surface 40. The surfaces of the capacitor plates 12, 14 the surface 40 of the photoconductor belt 16 face toward one another. The capacitor plates 12, 14 preferably have the same effective plate area. The photoconductor belt 16 is the cooperating electrode of the capacitor plates 12, 14.

The first capacitor plate 12 and the cooperating electrode 16 form a first capacitor 13, and the second capacitor plate 14 and the cooperating electrode 16 form a second capacitor 15. Given the same effective area of the capacitor plates 12, 14 and the same distance of the capacitor plates 12, 14 from the cooperating electrode 16, the first capacitor 13 and the second capacitor 15 have the same capacitance when no toner layer 38 and no toner residues are present between the photoconductor belt 16 and the capacitor plates 12. The distance between the photoconductor belt 16 and the capacitor plates 12, 14 is pre-set to a value in the range between 0.2 and 10 mm. A switch unit 26 is provided for connecting the capacitor plate 12 to a voltage source (not shown) that is positive relative to the reference potential 18 in a first switch status and for connecting the capacitor plate 14 to a voltage source (not shown) that is negative relative to the reference potential 18 in said first switch status. The amounts of the voltages are the same.

In a second switch status, the switch unit 26 parts the connections to the voltage sources and short-circuits the two capacitor plates. The residual charge is supplied to a filter 28. The filtered signal is supplied to an amplifier 30 that hands the amplified signal over to an evaluation unit 32. The filter type as well as the corresponding filter parameters of the filter are pre-set dependent on the ambient condition and switching frequency of the switch unit 16, which preferably lies in the range between 300 kHz and 1 MHz. A band-pass filter is preferably utilized.

The filter 28, the amplifier 30 and the evaluation unit 32 form an evaluation arrangement 24 for determining the layer thickness of the toner layer 38. The evaluation unit 32 hands the measured result 36 over to a higher-ranking controller (not shown) that regulates the layer thickness of the toner layer 38 to a pre-set value with the assistance of the measured result 36. The evaluation unit 32 also generates a square-wave signal 34 that prescribes the switching frequency for the switch unit 26 with which the switching is implemented from the first into the second switch status and from the second switch status into the first switch status. The changes in capacitance of the capacitors 13, 15 when the toner layer 38 is conveyed through between the cooperating electrode 16 and the capacitor plates 12, 14 is explained in even greater detail later in conjunction with FIGS. 6 and 7.

Figure 2:
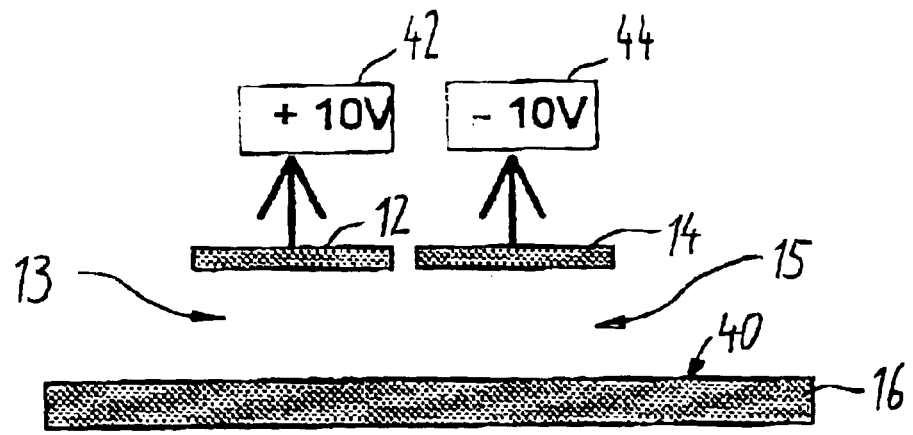
FIG. 2 shows a measurement arrangement of the apparatus according to FIG. 1 in a first switch status.

FIG. 2 shows the capacitor plates 12, 14 and the photoconductor belt 16 designed as a cooperating electrode in the first switch status. Identical elements have identical reference characters. In the first switch status, the first capacitor plate 12 is connected to a voltage supply unit 42 that offers a voltage of +10 V relative to the reference potential 18. The second capacitor plate 14 is electrically conductively connected to a second voltage supply unit 44 that offers a voltage of −10 V relative to the reference potential. Electrical charges are respectively supplied to the first and the second capacitor 13, 15 with the assistance of the voltage supply units 42, 44. The supplied charge is dependent on the respective capacitance of the capacitors 13, 15.

Figure 3:
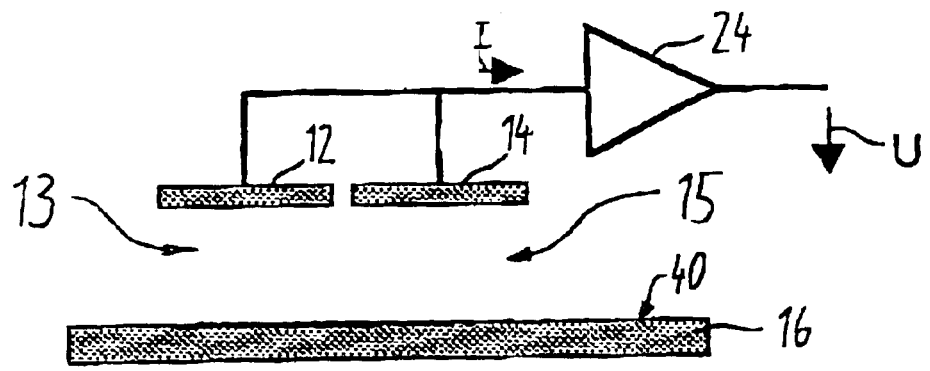
FIG. 3 shows the measurement arrangement in a second switch status.

FIG. 3 shows the capacitor plates 12, 14 and the photoconductor belt 16 fashioned as cooperating electrode in a second switch status. The capacitor plates 12, 14 are electrically connected to one another in the second switch status. In that the first capacitor 13 was supplied with positive charge carriers with the assistance of the voltage supply unit 42 and the second capacitor 15 was supplied with negative charge carriers with the assistance of the voltage supply unit 44, the resultant charge after an electrical connection of the two capacitor plates 12, 14 is the charge difference as a result of a different capacitance of the two capacitors 13, 15. The charge difference causes a current I that is supplied to the evaluation arrangement 24. The evaluation arrangement 24 generates a voltage signal from the current signal. As already explained in FIG. 1, the evaluation unit 32 determines the layer thickness of the toner layer 38 from this voltage signal corresponding to the difference in capacitance of the two capacitors 13, 15.

Given the same effective area of the capacitor plates 12, 14 and the same distance of these capacitor plates 12, 14 from the cooperating electrode 16, the charge difference is 0 when a toner layer is not situated between one of the plates and the cooperating electrode 16. When a toner layer 38 is situated between a capacitor plate 12, 14 and the cooperating electrode 16, then the capacitance of the capacitor 13, 15 changes. Due to the different capacitances of the capacitors 13, 15, a charge difference from which the layer thickness of the toner layer 38 is inferred is present at the time at which the toner layer 38 is not yet situated under the other capacitor 15 or, respectively, is no longer situated under the other capacitor 13.

The change in capacitance of the capacitors because of the toner layer 38 results from the change of the dielectric, i.e. from the change of the layered dielectric, of the respective capacitor when the toner layer 38 is conveyed through between the capacitor plate and the cooperating electrode. With apparatus 10, thus it is particularly changes in the layer thickness of the toner layer 38 as well as the layer thickness of the toner layer 38 itself that can be determined. The charge difference as a result of different capacitances of the capacitors 13, 15 is amplified with the assistance of the evaluation arrangement and converted into a voltage signal. Care must be exercised to see that no or only few outside charges falsify the measured result in the amplification and conversion. The voltage signal is then amplified and filtered with the assistance of the evaluation arrangement 24. Using this resultant signal, the evaluation unit 32 determines the layer thickness or the change in the layer thickness of the toner layer 38.

Figure 4:
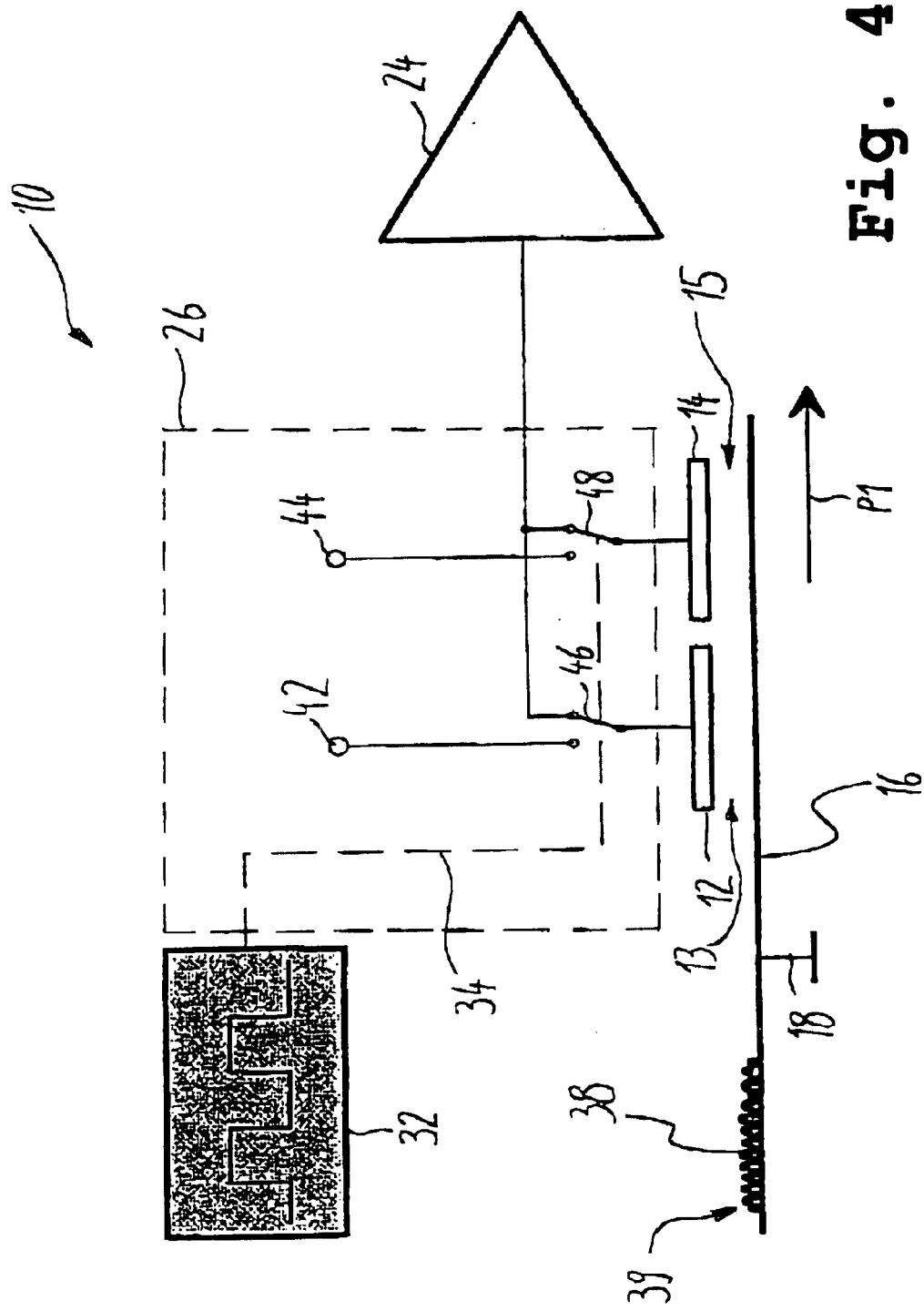
FIG. 4 illustrates an arrangement for the drive of capacitors for acquiring the layer thickness of a toner mark.

FIG. 4 shows an arrangement for the drive of the capacitors 13, 15 for acquiring the layer thickness of the toner layer 38. The switch unit 26 is supplied with a square-wave signal 34 that is generated by the evaluation unit 32. The switch unit 26 contains a first switchover 46 that, dependent on the switch status, connects the first capacitor plate 12 to the first voltage supply unit 42 in the first switch status and to the evaluation arrangement 24 in the second switch status. The switch unit 26 also contains a second switchover 48 that connects the second capacitor plate 14 to the voltage supply unit 44 in the first switch status and connects the second capacitor plate 14 to the evaluation unit 24 in the second switch status. The capacitor plates 12, 14 are short-circuited in the second switch status, so that a charge carrier compensation occurs and only the charge carrier difference of the capacitors 13, 15 is supplied to the evaluation arrangement 24.

The switch unit 26 switches over between the first and second switch status in conformity with the square-wave signal 34 supplied by the further evaluation unit 34. The square-wave signal 34 preferably has a frequency in the range between 300 kHz and 1 MHz. Due to the conveying motion of the photoconductor belt 16, the toner layer 38 of the toner mark 39 is conveyed forward in arrow direction P1 between the photoconductor belt 16 and the capacitor plates 12, 14. The switching of the two switching statuses is also referred to as switched capacitor technique.

Figure 5:
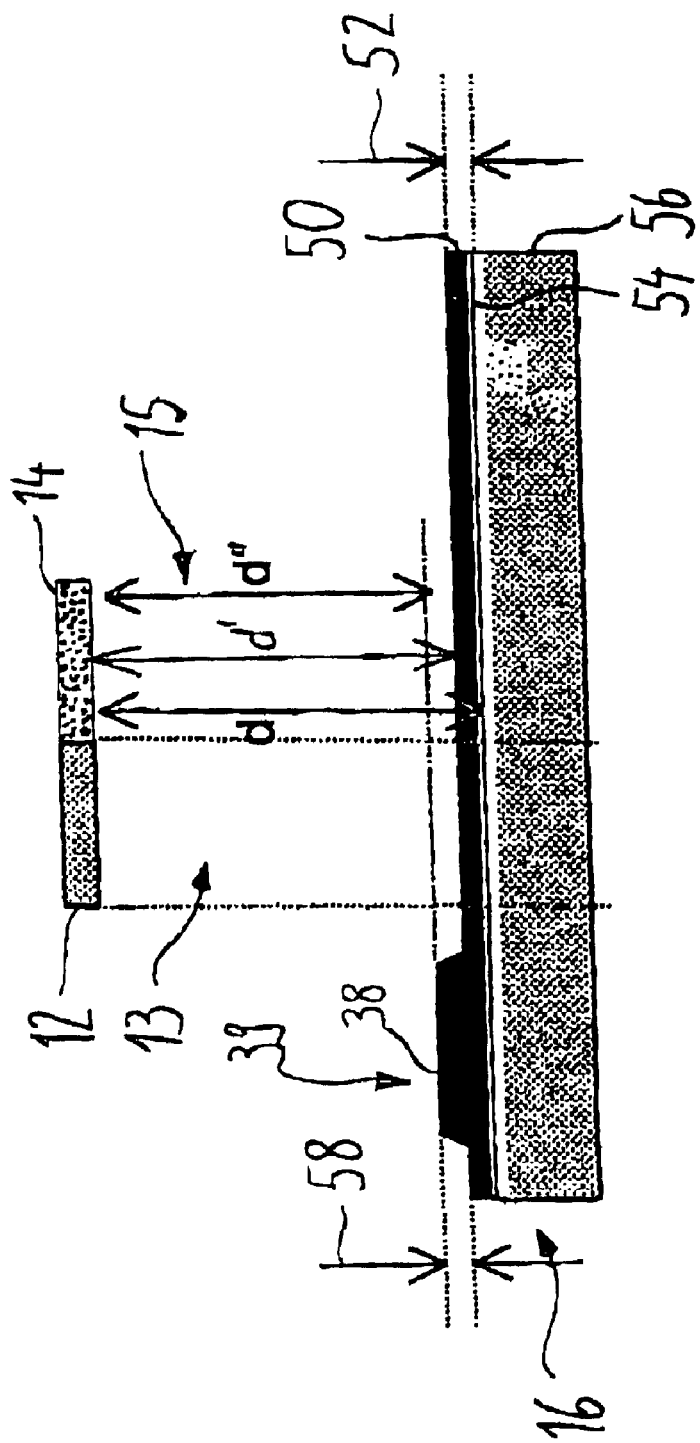
FIG. 5 is an arrangement for acquiring the layer thickness of the toner mark.

FIG. 5 shows the structure of the photoconductor belt 16 on which the toner layer 38 of the toner mark 39 is situated. The photoconductor belt 16 contains a carrier material 56 on which a metal layer 54 is located. For example, the metal layer 54 can be vapor-deposited on the carrier material. The metal layer 54 is electrically conductively connected to the reference potential 18 and forms the cooperating electrode of the capacitor plates 12, 14. A photoconductor layer 50 is located on the metal layer 54. In the illustration in FIG. 5, the thickness of the photoconductor layer is referenced 52. The photoconductor layer 52 forms the surface of the photoconductor belt 16. The toner layer 38 of the toner mark 39 is applied onto the photoconductor layer 50 with the assistance of an exposure and development unit (not shown). The layer thickness of the toner layer 38 is referenced 58 in FIG. 5.

The metal layer 54 and the first capacitor plate 12 form the first capacitor 13, and the metal layer 54 and the second capacitor plate 14 form the second capacitor 15. The overall capacitance of the first and of the second capacitor 13, 15 is respectively composed of the series-connected partial capacitances that is [sic] defined by the thickness 52 of the photoconductor layer 50 and the distance d' between the respective capacitor plate 12, 14 and the photoconductor layer 50. When the toner layer 38 of the toner mark 39 is situated between photoconductor 16 an a capacitor plate 12, 14, then the capacitance of the capacitor 13, 15 comprises the partial capacitances that are present due to the thickness 52 of the photoconductor layer 50, the thickness 58 of the toner layer 38 and the distance d' of the air layer between toner mark 39 and capacitor plate 12, 14. The overall capacitance of the respective capacitor thus changes in conformity with the thickness of the toner layer 38.

Figure 6:
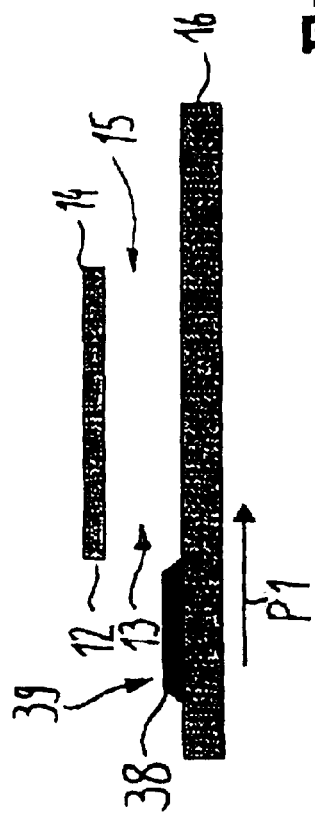
FIG. 6 is an arrangement comprising two capacitor plates past which the toner mark is conducted.

FIG. 6 shows the measurement arrangement for determining the layer thickness of the toner layer 38. The photoconductor belt 16 is moved in arrow direction P1, so that the toner layer 38 is transported forward between the capacitor plates 12, 14 and the photoconductor belt 16.

Figure 7:
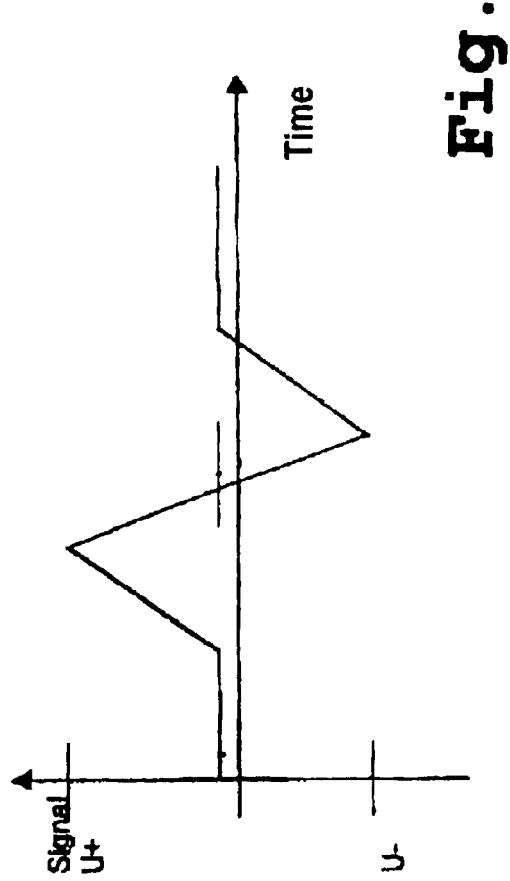
FIG. 7 is a voltage/time diagram with the signal curve of the measured results given the arrangement shown in FIG. 6.

FIG. 7 shows a voltage-time diagram with the basic signal curve of the measured result that is generated with the assistance of the evaluation arrangement 24 when the toner mark 39 is conveyed through given the measurement arrangement shown in FIG. 6. In the arrangement according to FIG. 6, the photoconductor belt 16 is conveyed through between the capacitor plates 12, 14 and the photoconductor belt 16 with a constant velocity in the range of 1 to 1.5 m/s. The relative permeability of toner is greater than the relative permeability of air. As already mentioned, the toner layer 38 is conveyed into the air gap d' between a first capacitor plate 12 and the photoconductor belt 16 with the assistance of the photoconductor belt 16. As a result thereof, the capacitance of the first capacitor 13 is increased. The capacitance of the first capacitor 13 increases until the toner layer 38 covers the largest possible effective area of the first capacitor 13.

The voltage signal that is generated by the evaluation arrangement 24 and that is shown in the diagram illustrated in FIG. 7 increases from 0 Volts up to the maximum U+ with increasing capacitance of the first capacitor 13. Due to the continuous conveying motion of the photoconductor belt 16, the toner layer 38 is conveyed into the air gap between the second capacitor plate 14 and the photoconductor belt 16 and is simultaneously conveyed out of the air gap between first capacitor plate 12 and photoconductor belt. Given the apparatus according to FIG. 6, the capacitance of the second capacitor 15 increases to the same extent that the capacitance of the first capacitor 13 decreases. The negative rise of the output signal of the evaluation arrangement 24 is thus approximately twice as great as given a mere conveying of the toner layer 38 out of the first capacitor 13 or given a mere conveying of the toner layer 38 into the second capacitor 15.

When the toner layer 38 has then been completely conveyed out of the first capacitor 13 and this toner layer 38 covers the largest possible effective area of the second capacitor 15, then the evaluation arrangement 24 outputs a voltage signal U− Subsequently, the toner layer 38 is conveyed out of the second capacitor 15, as a result thereof the voltage signal output by the evaluation arrangement 24 rises continuously from the value U− to 0 until the toner layer 38 has been conveyed out of the second capacitor 15. However, a change of the thickness 52 of the photoconductor layer 50, a change of the distance between metal layer and capacitor plates 12, 14 as well as a change of the dielectric between the capacitor plates 12, 14 and the photoconductor belt 16 can also be determined with the assistance of this apparatus. As a result thereof, for example, the photoconductor layer 50 of the photoconductor belt 16 or the adjustment of the capacitor plates 12, 14 can also be checked.

When the toner layer 38 is conveyed through between the capacitor plates 12, 14 and the photoconductor belt 16, a part of the air situated in the air gap d' is replaced by the toner layer 38. The capacitors 13, 15 thus contain a layered dielectric. The equivalent circuit diagram of the first and of the second capacitor 13, 15 derives from a series circuit of respectively three individual capacitances. The effective area of these individual capacitances is the area of the capacitor plate 12 or, respectively, 14. The first partial capacitance derives from the distance d" between the toner layer 38 and the capacitor plate 12 that is filled with air. The second partial capacitance derives from the thickness 58 of the toner layer 38, and the third partial capacitance derives from the thickness 52 of the photoconductor layer 50 as well as from the dielectric constant of this photoconductor layer 50. The overall capacitance of the first or, respectively, of the second capacitor 12, 14 thus derives from the following equation:

$$1/C_{Overall} = 1/C_{Air} + 1/C_{Photoconductor} + 1/C_{Toner},$$

whereby $C_{Overall}$ is the overall capacitance of the first or, respectively, of the second capacitor;

$C_{Air}$ is the capacitance of the air layer between toner layer 38 and capacitor plate 12 or, respectively, 14;

$C_{Photoconductor}$ is the capacitance of the photoconductor layer; and $C_{Toner}$ is the capacitance of the toner layer 38.

The respective overall capacitance of the first or, respectively, second capacitor 13, 15 is thus dependent on the absolute distance of the capacitor plates 12, 14 from the metal layer 54 that forms the cooperating electrode, on the layer thickness 50 of the photoconductor and on the layer thickness 58 of the toner layer 38. Topical changes in the layer thickness of the carrier material of the photoconductor belt that influence the distance d between metal layer and capacitor plates 12, 14 influence the overall capacitance of the first and of the second capacitor 13, 15. The apparatus can thus also be used for quality control of the surface of photoconductors and transfer belts.

Figure 8:
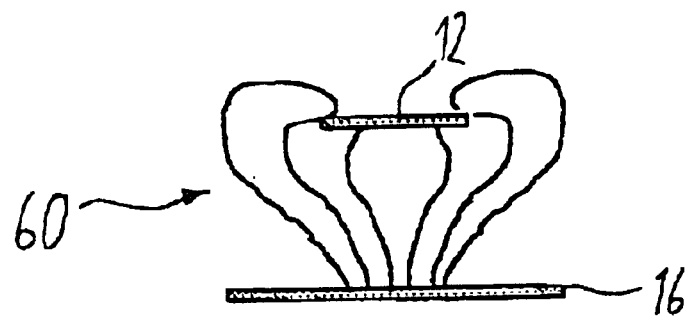
FIG. 8 is a plate capacitor with the field line course of the electrical field.

FIG. 8 shows the field line course 60 between photoconductor belt 16 and the capacitor plate 12. A non-uniform electrical field forms between the photoconductor belt 16 and the capacitor plate 12, particularly in the edge regions of the capacitor plate 12. Measurement errors in the determination of the layer thickness of the toner layer 38 occur due to such a non-uniform electrical field.

Figure 9:
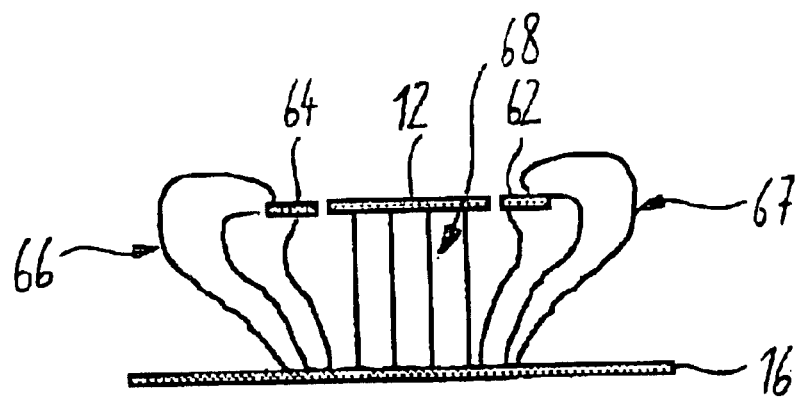
FIG. 9 shows a plate capacitor with protective electrode with the field line course of the electrical field.

FIG. 9 shows the capacitor plate 12 and the photoconductor belt 16 used as a cooperating electrode. Protective electrodes 62, 64 are arranged next to the capacitor plate. Non-uniform fields 66, 67 form between the protective electrodes 62, 64 and the cooperating electrode. The effect of the protective electrodes is that a homogeneous electrical field 68 can be formed between the capacitor plate 12 and the photoconductor belt 16. Measurement errors as a consequence of non-uniform electrical fields are precluded as a result thereof. Protective electrodes 62, 64 can also be arranged next to the capacitor plate in the same way.

Figure 10:
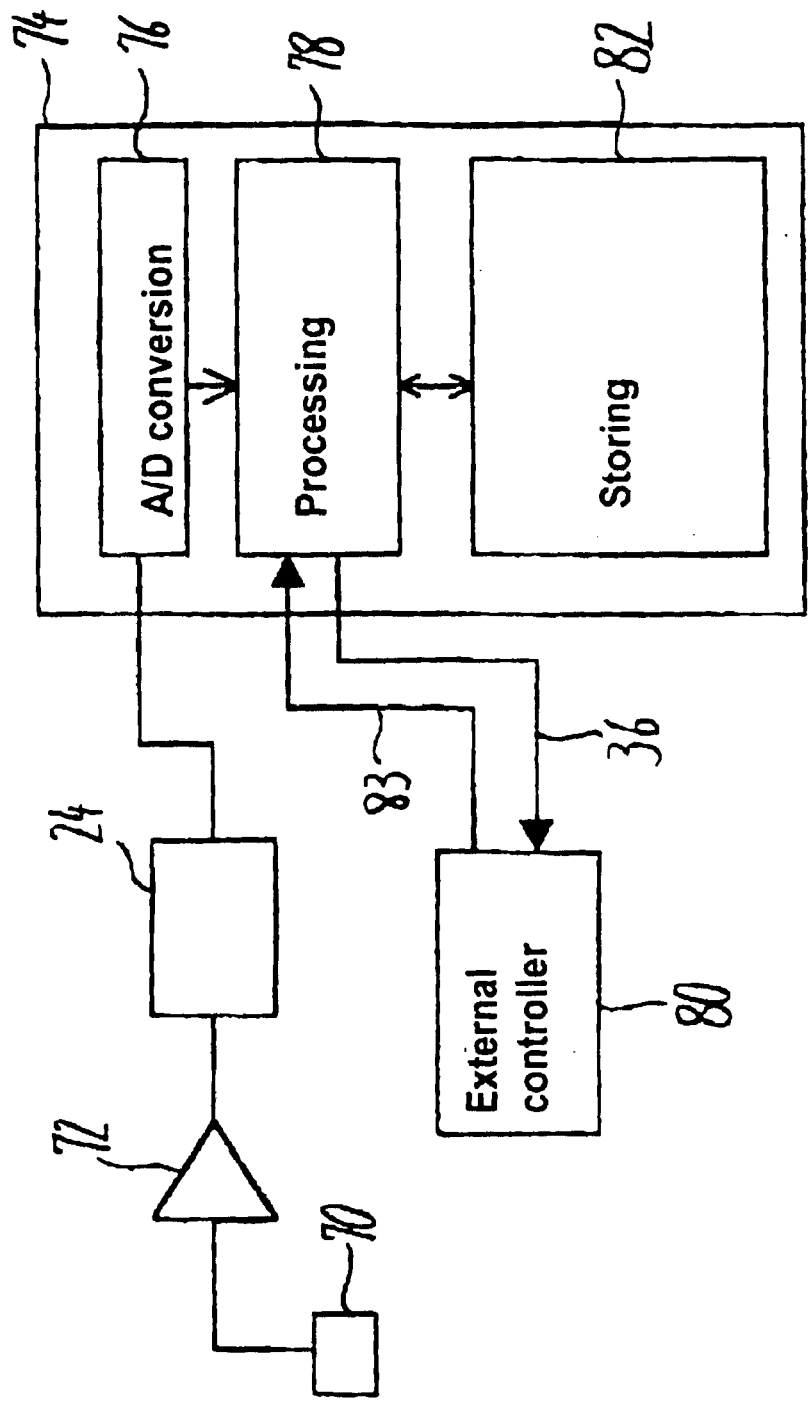
FIG. 10 is a block circuit diagram that shows the further-processing of the sensor signal in a printer or copier.

FIG. 10 shows a block circuit diagram for acquiring and evaluating the layer thickness 58 of a toner layer 38 in a printer or copier. A sensor arrangement 70 contains the capacitor plates 12, 14, the cooperating electrode 16 and a switch unit 26. A conversion unit 72 generates a voltage signal from a charge difference of the two capacitors 13, 15 of the sensor unit 70. This voltage signal is filtered and amplified with the assistance of the evaluation arrangement 24. The filtered and amplified signal is supplied to a digital signal processor 74. This digital signal processor 74 implements an analog-to-digital conversion 76. After the analog-to-digital conversion, the digital signal processor 74 implements an evaluation of the converted data with the assistance of a processing unit 78 and determines a measured result 36 that it hands over to an external controller 80 for further-processing.

The digital signal processor 74 stores current measured values as well as comparison values with the assistance of a memory unit 82. The digital signal processor 74 uses the comparison values in the processing of the current measured values in the processing unit 78. These comparison values are taken into consideration in the determination of the measured result 36. Further, the external controller 80 provides the digital signal processor 74 with default values 83 that, for example, contain device parameters and parameters of the toner as well as of the carrier material. The external controller 80 also informs the digital signal processor 74 of various operating phases and an initialization of the digital signal processor 74.

Figure 11:
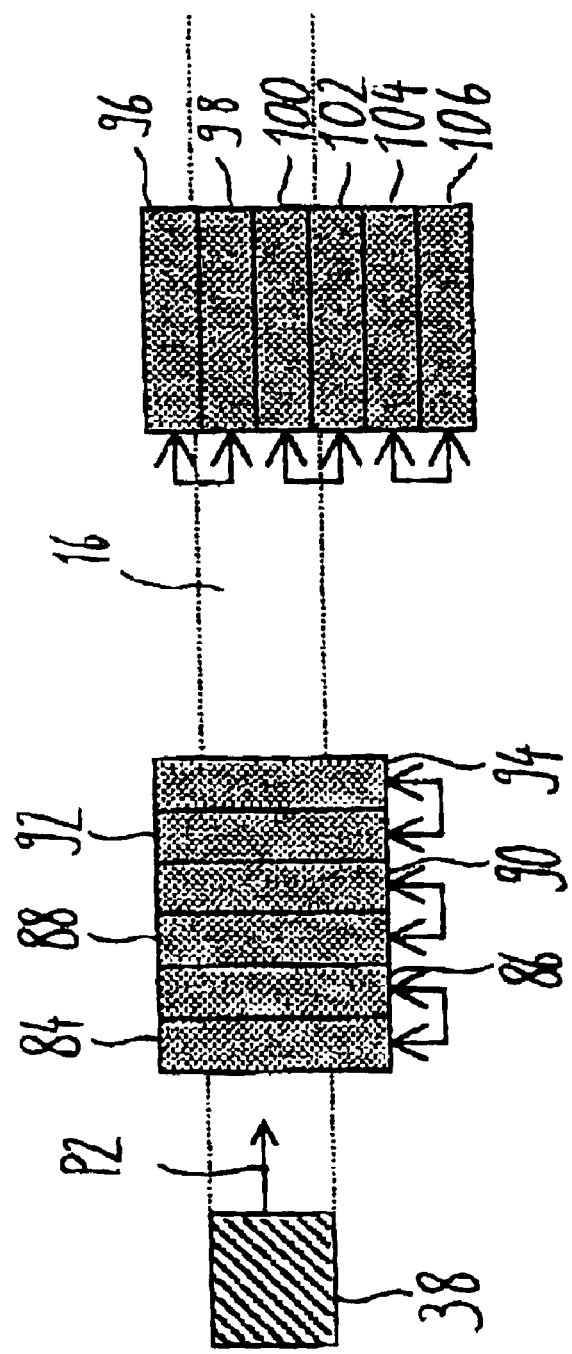
FIG. 11 is an arrangement with capacitor plates arranged in pairs showing their position relative to the moving direction of the toner mark.

FIG. 11 shows another exemplary embodiment for acquiring the layer thickness 58 of the toner layer 38. The toner layer 38 is situated on the photoconductor belt 16 that serves as cooperating electrode for capacitor plates and that is driven with the assistance of a drive unit (not shown). The photoconductor belt 16 is preferably continuously driven. The toner layer 38 is transported in the arrow direction of the arrow P2 with the assistance of the photoconductor belt 16. Capacitor plates 84 through 94 are arranged at a distance from the photoconductor belt 16 transversely relative to the moving direction of the toner mark 39, and capacitor plates 96 through 108 are along the moving direction of the toner mark 39. The capacitor plates 84 through 106 respectively form a capacitor with the cooperating electrode. The capacitor plates 84, 86; 88, 90; 92, 94; 96, 98; 100, 102; 104, 106 respectively form a plate pair that is respectively evaluated, as already described with reference to the example of the capacitor plates 12, 14 in conjunction with FIGS. 1 through 10. The capacitor plate pairs respectively form a sensor surface. The combination of a plurality of sensor surfaces in moving direction of the toner mark 39 serves for the more exact determination of the position of the toner mark 39 on the photoconductor belt 16. When a plurality of sensor surfaces are arranged transversely relative to the moving direction of the toner mark 39, the transport velocity of the toner mark 39 can also be determined in a simple way.

Figure 12:
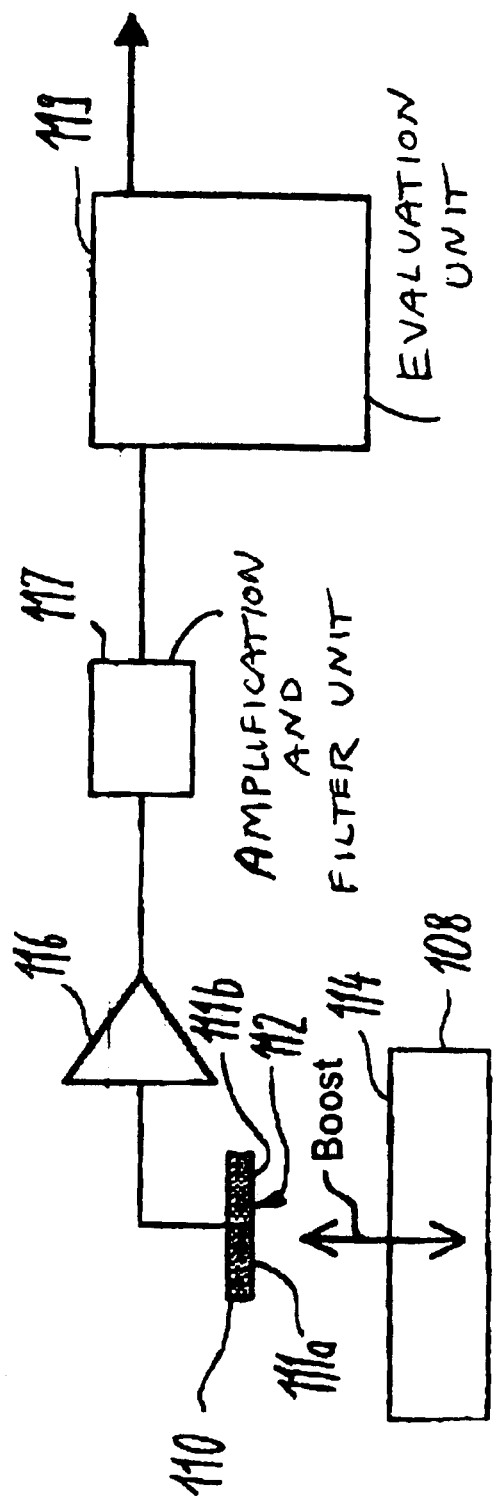
FIG. 12 is an arrangement for frequency analysis of the oscillation of a metallic surface.

FIG. 12 shows an arrangement for the frequency analysis of the oscillation of a metallic surface 114 or an article 108. The distance between a sensor surface 112 of the sensor arrangement 110 and the surface 114 of the article 108 is determined with the assistance of the measurement principle already described in conjunction with FIGS. 2, 3 with the assistance of a sensor arrangement 110 that contains two capacitor plates 111a, 111b. The sensor surface 112 is aligned parallel to the surface 114 of the article 108. An evaluation circuit 116 converts the sensor signal into a voltage signal. The voltage signal is a measure of the change in capacitance of the capacitors contained in the sensor arrangement 110. The voltage signal is supplied to an amplification and filter unit 117 that generates a filtered and amplified signal from this supplied signal and supplies it to an evaluation unit 119, preferably a digital signal processor. The evaluation unit 119 serves for the acquisition, storing and evaluation of the supplied measured values. The capacitances of two capacitors contained in the sensor arrangement 110 changes [sic] in the same way given an oscillation of the surface. For frequency analysis of the oscillation of the metallic surface 114, the evaluation unit 118 compares successively determined measured values of the sensor arrangement 110.

In other embodiments of the exemplary embodiment, the sensor arrangement 110 can also contain only one capacitor. The change in capacitance of a plurality of successive measured values can likewise be used for the frequency analysis of the oscillation of the metallic surface 114, as was already described for the two capacitors of the sensor arrangement 110.

Figure 13:
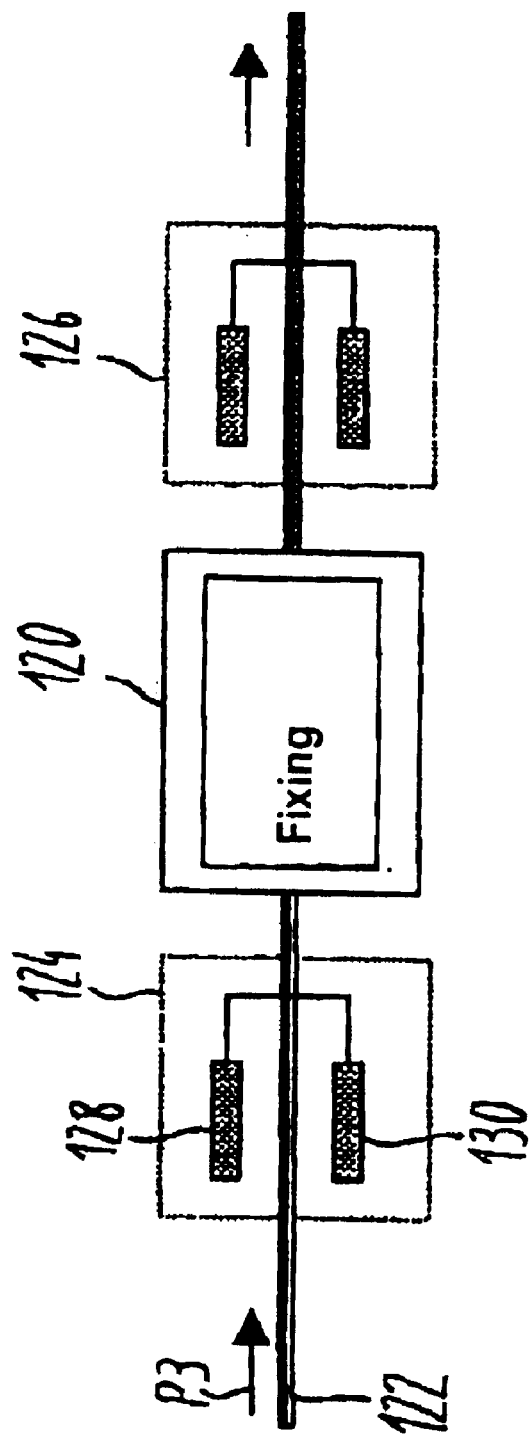
FIG. 13 is an arrangement for acquiring the paper moisture preceding and following a fixing unit.

FIG. 13 shows an arrangement for determining and regulating the fixing performance of a fixing unit 120. A toner image (not shown) that is situated on a paper web 122 is fixed on this paper web with the assistance of the fixing unit 120. In the fixing event, moisture is withdrawn from the paper web 122 by the fixing energy supplied by the fixing unit 120. The paper moisture of the paper web 122 before the fixing event is acquired with the assistance of a first sensor arrangement 124, and the paper moisture of the paper web 122 after the fixing event is acquired with the assistance of a second sensor arrangement 126. The paper web 122 is continuously conveyed through the fixing unit 120 in the arrow direction of the arrow P3.

The first sensor arrangement 124 has a first capacitor plate 128 and a second capacitor plate 130 between which the paper web 122 is transported forward. The capacitor plates 128, 130 form a capacitor, whereby the capacitor plate 130 is implemented as cooperating electrode. The paper web 122 and the air between the capacitor plates 128, 130 of the capacitor of the first sensor arrangement 124 form a layered dielectric. Given constant ambient conditions, particularly given constant atmospheric humidity, the capacitance of the capacitor of the first sensor arrangement 124 is dependent on the moisture content of the paper web 122 situated between the capacitor plates 128, 130. As a result thereof, the moisture content of the paper web 122 can be exactly determined with the assistance of the first sensor arrangement 124 preceding the fixing unit. The second sensor arrangement 126 is constructed in the same way as the first sensor arrangement 124. The moisture content of the paper web 122 following the fixing event is determined with the assistance of the second sensor arrangement 126. An evaluation unit (not shown) forms the difference between the identified moisture contents. This difference as well as the absolute moisture content of the paper web 122 before the fixing can, for example, be utilized for regulating the fixing energy generated for the fixing by the fixing unit 120.

Figure 14:
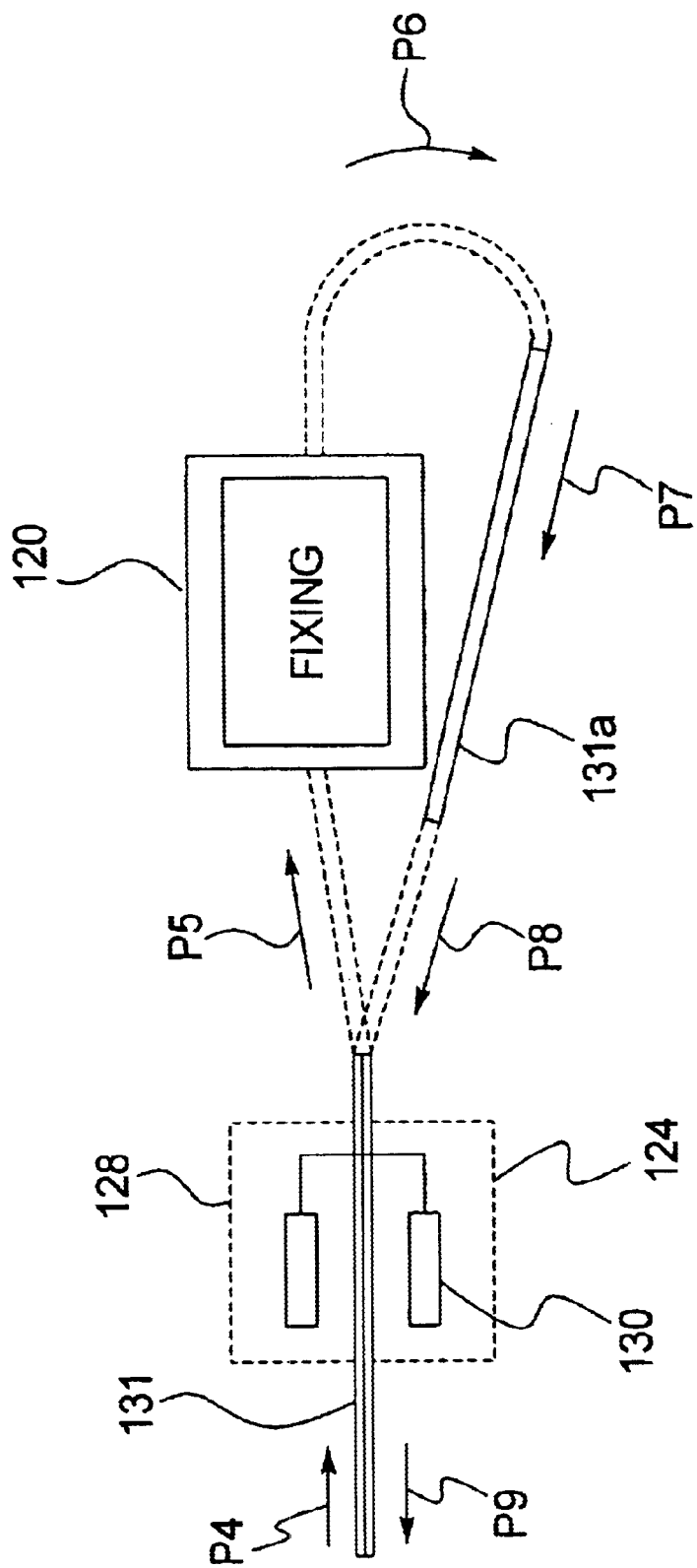
FIG. 14 is an apparatus for acquiring the moisture content of a single sheet preceding and following the fixing.

FIG. 14 shows an arrangement for determining the moisture content of single sheets 131 before and after fixing by the fixing unit 120. Identical elements have identical reference characters. A single sheet 131 is supplied to the fixing unit 120 in arrow direction P4 and P5. The sensor arrangement 124 determines the moisture content of the single sheet 131 before the fixing. After the fixing with the assistance of the fixing unit 120, the single sheet 131 is further-transported in arrow direction P6, P7, P8 and P9, whereby it is re-supplied to the sensor arrangement 124. The fixed single sheet is referenced with reference character 131a in FIG. 14. The sensor arrangement 124 determines the moisture content of the single sheet 131a after the fixing. The moisture difference of the single sheet 131 before the fixing and of the fixed single sheet 131a as well as the absolute moisture content of the single sheet 131 before the fixing can be used by a control unit (not shown) for regulating the fixing performance of the fixing unit 120.

Figure 15:
FIG. 15 shows a first sensor surface arrangement.
Figure 16:
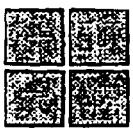
FIG. 16 shows a second sensor surface arrangement.
Figure 17:
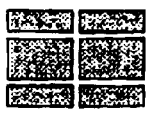
FIG. 17 shows a third sensor surface arrangement.

FIGS. 15 through 21 show possible versions of arrangements of capacitor plates that can be utilized as sensor surfaces for arrangements described in FIGS. 1 through 14. FIG. 15 thereby shows a basic implementation of a sensor surface that contains two capacitor plates. FIG. 16 shows a sensor surface that contains four quadratic sensor surfaces. FIG. 17 shows a sensor surface that likewise contains four sensor surfaces, whereby one plate pair is divided.

Figure 18:
FIG. 18 shows a fourth sensor surface arrangement.

FIG. 18 shows a sensor surface similar to the sensor surface of FIG. 15. Differing from the sensor surface according to FIG. 15, the sensor surface shown in FIG. 18 has a protective electrode 136 that surrounds the capacitor plates 132, 134. As already described in the comments abut FIG. 9, a uniform formation of the electrical field of the capacitors of the capacitor plates 132, 134 is assured by means of the protective electrode 136.

Figure 19:
FIG. 19 shows a fifth sensor surface arrangement.

FIG. 19 shows a sensor surface with capacitor plates 138, 140 that mesh with one another. When acquiring a toner mark with the assistance of a sensor surface with meshed capacitor plates, a sensor signal having local maximums and minimums that provide information about the nature of the toner particle layer is generated as a result of the meshing. Measuring errors can also be recognized and evaluated by means of this arrangement.

Figure 20:
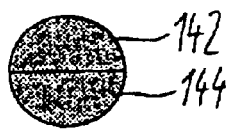
FIG. 20 shows a sixth sensor surface arrangement.

FIG. 20 shows two semicircular capacitor plates 142, 144 that are arranged such that the sensor surface yields a circular surface.

Figure 21:
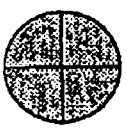
FIG. 21 shows a seventh sensor surface arrangement.

FIG. 21 shows four capacitor plates that respectively form a quarter-circle and together form a circular sensor surface. The sensor surfaces of FIGS. 20 and 21 are particularly suited for acquiring circular toner marks 39.

Figure 22:
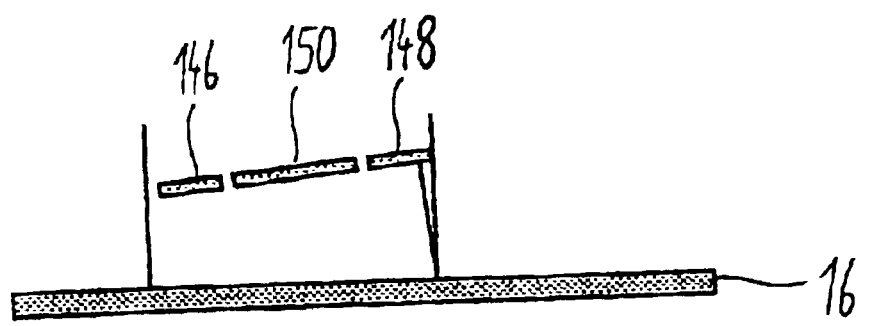
FIG. 22 shows an arrangement of the sensor surface with cooperating electrode.

FIG. 22 shows the sensor surface according to FIG. 17 as a sectional view through three of these capacitor plates in an arrangement over the photoconductor belt 16. The employment of four capacitor plates enables a reference measurement in addition to the actual measurement in order to be able to detect and correct influences of the carrier material on the measured result. Given the sensor surface shown in FIG. 17, a division of the capacitor plate pair for the reference measurement onto two plate pairs occurs, respectively one capacitor plate pair 146 thereof being arranged to the left and one capacitor plate pair 148 being arranged to the right of the main plate pair 150. This arrangement also enables a correction of a measurement error that occurs given what is not an exactly parallel alignment of the capacitor plates relative to the cooperating electrode, as shown in the arrangement according to FIG. 22. A protective electrode similar to the protective electrode 136 shown in FIG. 18 can be additionally provided in all sensor shapes according to FIGS. 15 through 17 and 19 through 21.

Figure 23:
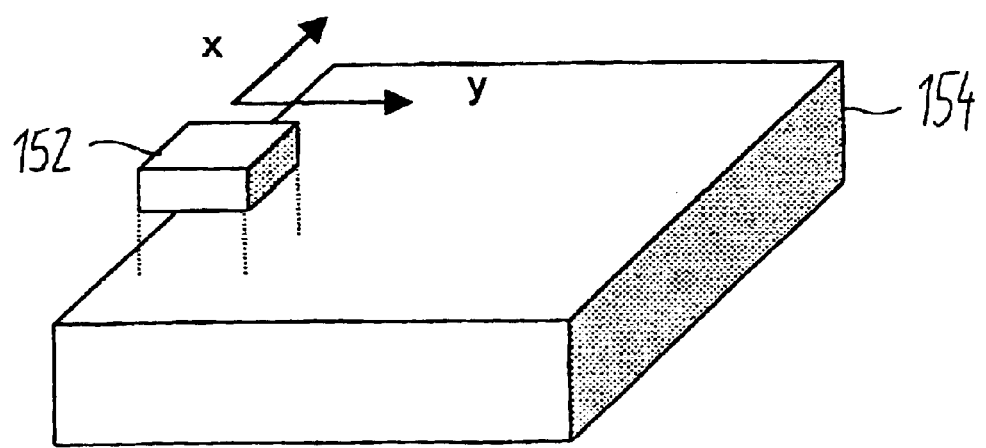
FIG. 23 illustrates a positioning of a sensor relative to the test subject.

FIG. 23 shows an arrangement for positioning a sensor 152. The sensor 152 is arranged over a test subject 154. The x-position and y-position of the sensor 152 is supplied to a controller (not shown). When a change of this position is needed, the controller outputs control signals to a positioning device that changes the position of the sensor 152 relative to the test subject 154, particularly in x-direction and y-direction. Such a positioning device can, for example, contain stepping motors and a spindle drive. Irregularities of the surface of the test subject 154 can, for example, be acquired with the assistance of this arrangement.

Figure 24:
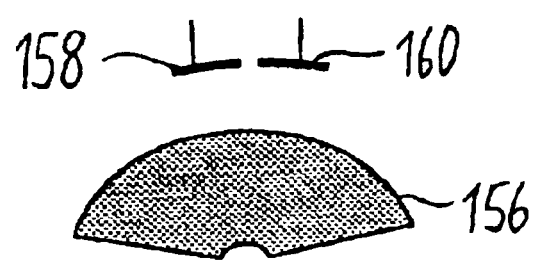
FIG. 24 illustrates a curved cooperating electrode, whereby the capacitor plates are curves in conformity with the course of the cooperating electrode.

FIG. 24 shows a side view of a curved sensor surface for measuring curved sensor surfaces. Given non-planar cooperating electrodes that, for example, have cylindrical surfaces 156, it is advantageous to fashion the capacitor plates 158, 160 of the sensor surface curved such that they follow the course of the surface 156 of the cooperating electrode. Measurement errors can be avoided as a result thereof. Particularly given drum-shaped cooperating electrodes that have a cylindrical surface 156, a curvature of the capacitor plates 158, 160 of the sensor surface is advantageous that corresponds to the circular path around the longitudinal axis of the cooperating electrode on which the capacitor plates 158, 160 are to be arranged.

Figure 25:
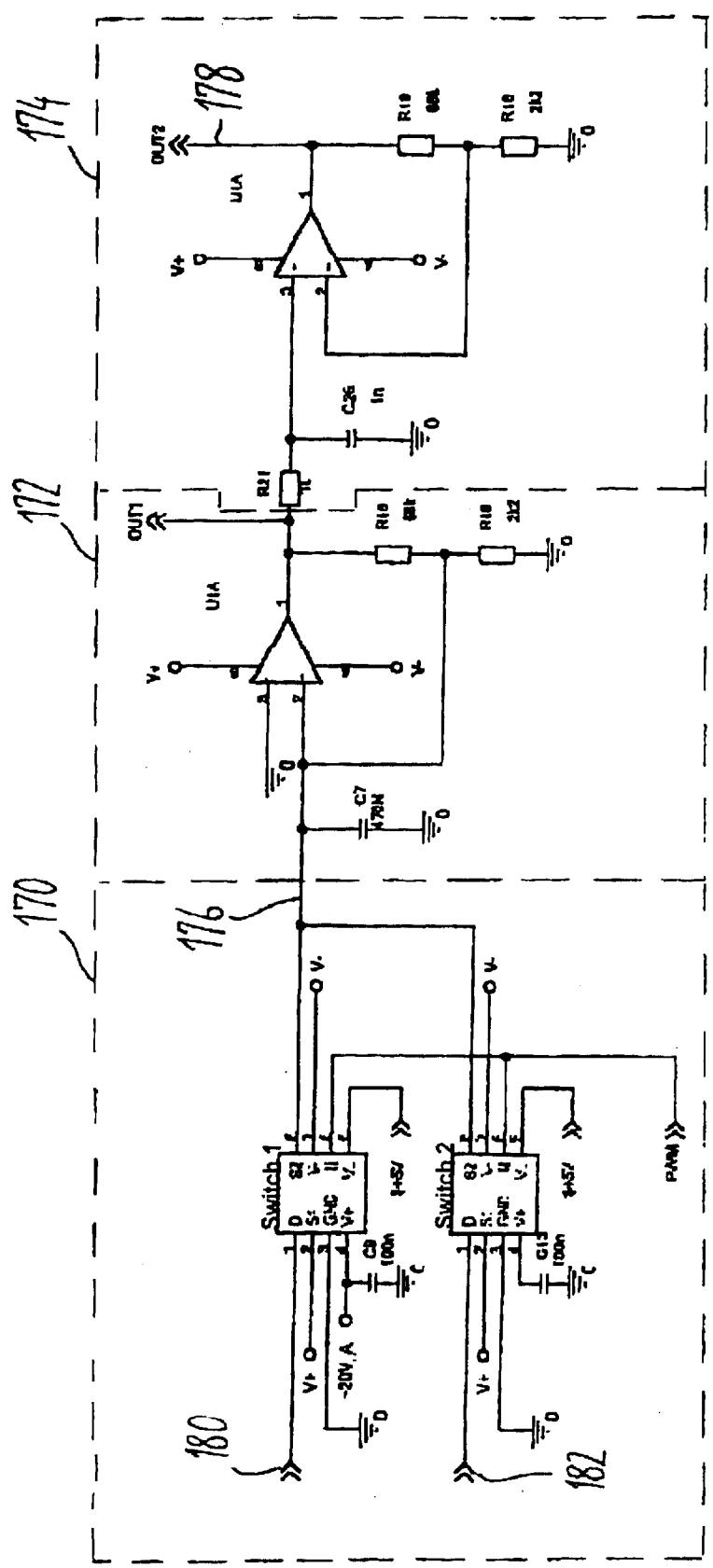
FIG. 25 shows a circuit diagram for the drive and evaluation of an apparatus with a capacitative sensor that contains two capacitor plates.

FIG. 25 shows a circuit diagram for the drive of a sensor arrangement that contains two capacitor plates. A drive unit 170 is provided for driving the two capacitors. the drive unit 170 switches between the first and the second switch status, as already explained in the description of FIGS. 2 and 3. The drive unit 170 conducts a sensor signal 176 to a first amplifier stage 172. The sensor signal 176 is formed from the charge difference of the two capacitors. The first amplifier stage 172 amplifies this signal and converts it into a voltage signal. This voltage signal is supplied to the second amplifier stage 174 that generates a second amplified voltage signal 178 that is supplied to a further evaluation unit, for example a digital signal processor. The capacitor plates are connected to the terminals 180, 182 of the drive unit 170.

The switchover devices described in the exemplary embodiments can also be replaced in other exemplary embodiments by respectively two switch pairs that are interlocked such with one another that only one switch pair is respectively closed.

In other exemplary embodiments, sensor surfaces are also conceivable that have different geometries and different dimensions in relationship to the toner layer or carrier material to be detected. Given, for example, a variation of the dimensions of the capacitor plates 12, 14 shown in FIG. 6, thus, a curve can be generated that is different from the diagram shown in FIG. 7. For example, round or elliptical sensor surfaces are meaningful and possible given round toner marks. Given inter-engaging meshing of the capacitor plates of the sensor surfaces, fluctuations over the range of measurement are compensated.

The devices and arrangements described in FIGS. 1 through 25 and that serve for the drive and evaluation of a capacitative sensor can also be utilized for quality control or for regulating the coating of metallic articles with electrically non-conductive materials. These devices can also be utilized for detecting contaminants and agglomerations on metallic articles. Embodiments for all described devices are possible wherein the test subject is stationarily arranged and the sensor is moved, as was already described in conjunction with FIG. 23. Given non-conductive carrier material, a cooperating electrode is to be arranged behind the carrier material, as seen from the direction of the sensor surface. In other embodiments of the invention, reference measured values are identified that are used in the evaluation of current measured values.

A guide mechanism can be provided for the guidance of the photoconductor belt 16, this assuring a quiet belt guidance in the region of the capacitor plates 12, 14 and, thus, a constant distance between belt and capacitor plates 12, 14. Such a guide mechanism can, for example, be implemented as a guide block that is arranged behind the photoconductor belt 16 as seen from the direction of the capacitor plates and over which the photoconductor belt 16 is conducted.

While a preferred embodiment has been illustrated and described in detail in the drawings and foregoing description, the same is to be considered as illustrative and not restrictive in character, it being understood that only the preferred embodiment has been shown and described and that all changes and modifications that come within the spirit of the invention both now or in the future are desired to be protected.

We claim as our invention:

1. An apparatus for acquiring a nature of a toner particle layer in a printer or copier, comprising:
    a first capacitor plate and a second capacitor plate arranged next to one another and lying opposite at least one cooperating electrode to form a first capacitor and a second capacitor;
    a layer containing toner particles arranged in a region between the two capacitor plates and the cooperating electrode;
    the two capacitors being charged with voltages opposite one another by a switch unit in a first switch status; and
    the first and second capacitor plates being electrically connected to one another by the switch unit in a second switch status so that a remaining charge after a charge compensation is determined and conclusions about the nature of the toner layer are drawn therefrom.

2. The apparatus according to claim 1 wherein the remaining charge generates a current that serves as signal values.

3. The apparatus according to claim 2 wherein means are provided for converting the current signal values into a voltage signal value.

4. The apparatus according to claim 2 wherein a signal processing unit amplifies the signal values generated from the remaining charge and filters it with assistance of a band-pass filter.

5. The apparatus according to claim 1 wherein a signal processing unit determines at least one of toner density and thickness of the layer containing toner particles.

6. The apparatus according to claim 5 wherein the signal processing unit determines at least one of toner density and thickness of the toner layer with the assistance of pre-set comparison values.

7. The apparatus according to claim 1 wherein a duration of the first and of the second switch statuses lie in the range between 10 and 90% of an overall duration of both switch statuses; and the switch statuses are switched with a frequency between 300 kHz and 3 MHz.

8. The apparatus according to claim 1 wherein the layer containing the toner particles is arranged on a carrier element.

9. The apparatus according to claim 8 wherein the layer on the carrier element is transported forward between the capacitor plates and the cooperating electrode.

10. The apparatus according to claim 8 wherein the carrier element contains conductive material; and the carrier element forms the cooperating electrode.

11. The apparatus according to claim 8 wherein the carrier element is one of a belt and a drum.

12. The apparatus according to claim 11 wherein the belt is one of a photoconductor belt and a transfer belt; and the drum is one of a photoconductor drum and an applicator drum.

13. The apparatus according to claim 11 wherein guide elements that assure a constant distance between the capacitor plates and the belt are arranged opposite the capacitor plates.

14. The apparatus according to claim 11 wherein in a first operating phase of the printer or copier, a signal processing unit acquires the signal values of the remaining charge of an entire belt revolution or an entire drum revolution cleaned of toner particles, or of the drum cleaned of toner particles and stores them together with data about allocation of the signal values to the respective drum or belt position in a memory area of the signal processing unit.

15. The apparatus according to claim 14 wherein in a second operating phase of the printer or copier, the signal processing unit forms a difference between current and stored signal values for each stored drum or belt position, the signal processing unit determining the nature of the toner layer with the assistance of the difference.

16. The apparatus according to claim 15 wherein the first operating phase is activated after the printer or copier is turned on; and the second operating phase is automatically activated after determination of the signal values of at least one of the drum and belt revolution.

17. The apparatus according to claim 2 wherein control of at least one of the apparatus and signal processing of the signal values occurs with assistance of a digital signal processor.

18. The apparatus according to claim 1 wherein the capacitors are driven by a switched capacitor method.

19. A method for acquiring a nature of a toner particle layer in a printer or copier, comprising the steps of:
    arranging a first capacitor plate and a second capacitor plate next to one another and lying opposite at least one cooperating electrode to form a first capacitor and a second capacitor;
    arranging a layer that contains toner particles in a region between the two capacitor plates and the cooperating electrode;
    charging the two capacitors with voltages opposite one another in a first switch status; and
    electrically connecting the first and the second capacitor plates to one another in a second switch status, determining a remaining charge after a charge compensation, and drawing conclusions about the nature of the toner layer therefrom.

* * * * *